United States Patent [19]

Agbodoe

[11] Patent Number: 5,318,509

[45] Date of Patent: Jun. 7, 1994

[54] HEAD CLAMP SAFETY LOCKING PIN

[75] Inventor: Victor B. Agbodoe, Boston, Mass.

[73] Assignee: Codman & Shurtleff, Inc., Randolph, Mass.

[21] Appl. No.: 44,355

[22] Filed: Apr. 7, 1993

[51] Int. Cl.⁵ ............................................. A61B 19/00
[52] U.S. Cl. ......................................... 602/32; 5/637; 5/640; 5/643; 602/33; 602/37; 602/36
[58] Field of Search .................. 119/729; 5/637, 640, 5/643, 622; 602/32, 33, 36, 37; 606/96

[56] References Cited

U.S. PATENT DOCUMENTS

| | | | |
|---|---|---|---|
| 2,966,383 | 12/1960 | Boetcker et al. | 311/10 |
| 3,099,441 | 7/1963 | Ries | 269/328 |
| 3,835,861 | 9/1974 | Kees et al. | 128/346 |
| 4,108,426 | 8/1978 | Lindstroem et al. | 269/328 |
| 4,169,478 | 10/1979 | Hickmann | 128/346 |
| 4,545,572 | 10/1985 | Day | 269/328 |

Primary Examiner—Richard J. Apley
Assistant Examiner—Beverly A. Meindl
Attorney, Agent, or Firm—Michael Q. Tatlow

[57] ABSTRACT

A surgical head clamp having two arms, one with a single head engaging pin and the second with two head engaging pins mounted on a bracket. The bracket is capable of being rotated to reposition the head. The operating knob which releases the bracket to allow rotation has a safety locking pin which prevents the inadvertent rotation of the bracket when the pin is in a locked position.

4 Claims, 4 Drawing Sheets

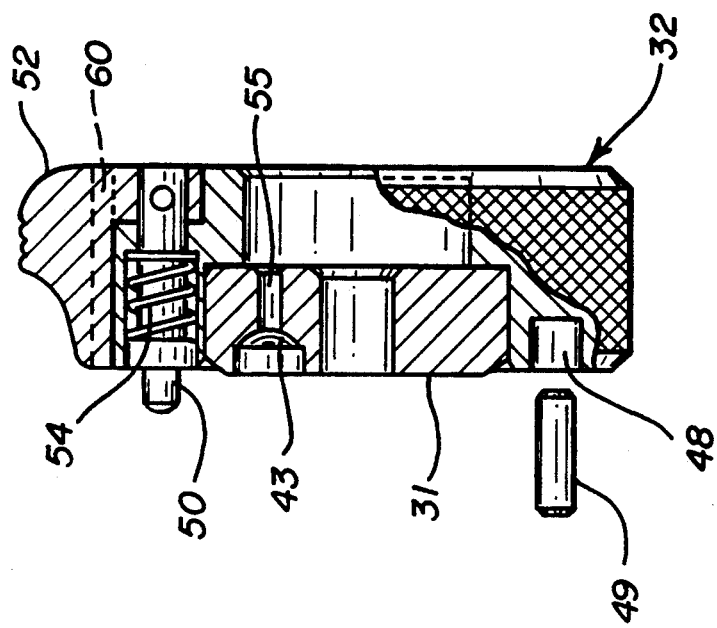
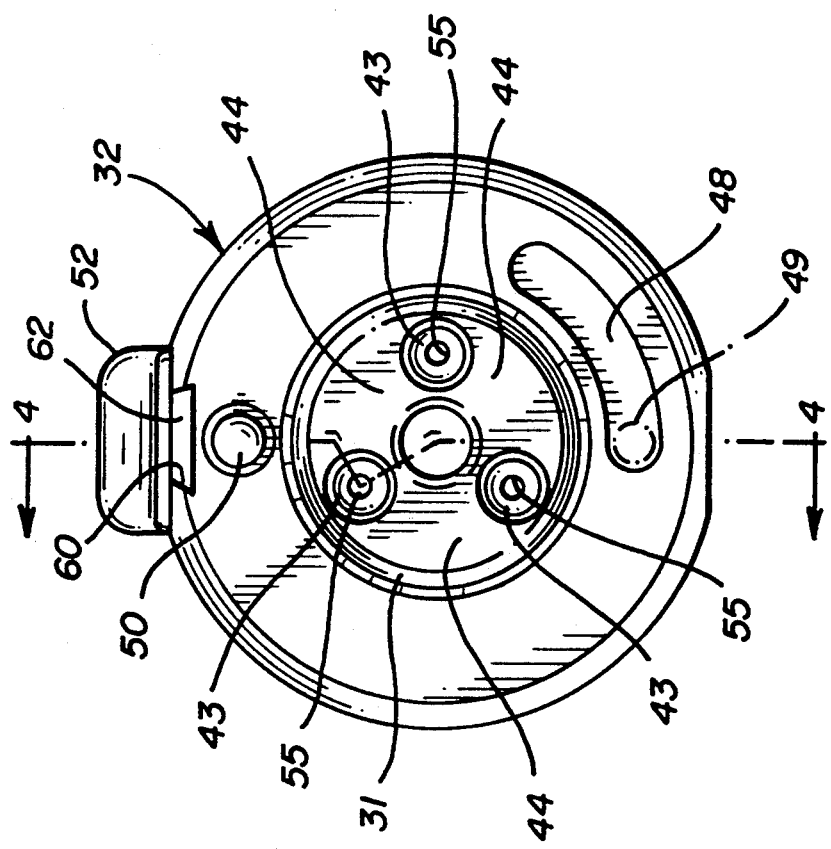

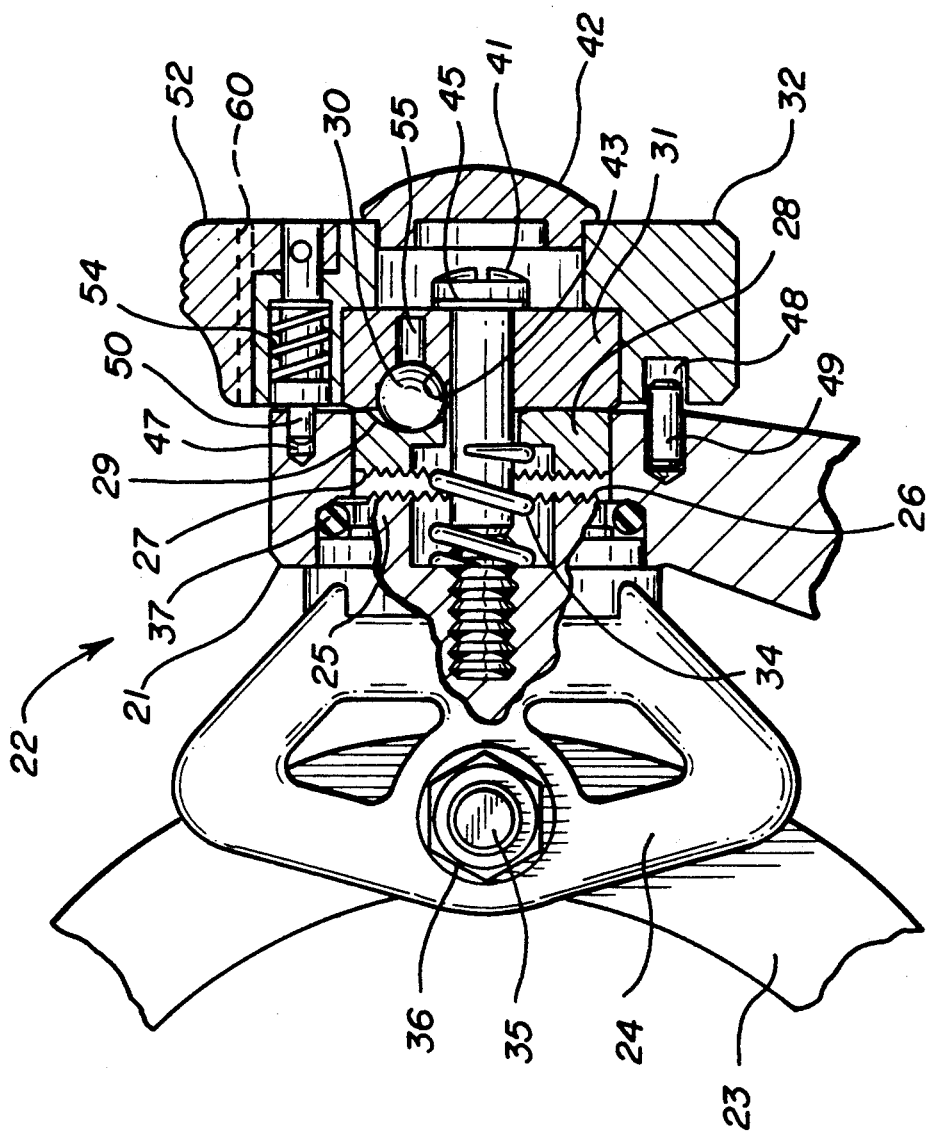

HEAD CLAMP SAFETY LOCKING PIN

The present invention relates to a skull clamp or surgical head clamp to hold the head of the patient in position for neurosurgical operations and for other procedures involving the patient's head.

BACKGROUND OF THE INVENTION

Surgical head clamps or skull clamps generally are provided with two types of mechanisms to hold the head in position. One type of clamps uses pads that are forced against the patient's head to hold the head in position. Examples of head clamps of this type are disclosed in U.S. Pat. Nos. 4,108,426 and 4,545,572.

A second type of head clamp uses a series of head engaging pins which engage the patient's skull at three points and provide positive anchorage of the head engaging pins into the skull. If the head engaging pins are held in a stable position, there is little likelihood that the skull will move relative to the head engaging pins during the surgical procedure.

The head clamp disclosed in U.S. Pat. No. 2,966,383 shows a three pin arrangement with the head engaging pins carried on hinged arms.

U.S. Pat. No. 3,099,441 discloses a surgical head clamp which contains two head engaging pins on a bracket supported by an arm and a third head engaging pin supported by another arm in the device. The two arms are brought together to adjust the space between the head engaging pins to fit the dimensions of the patient's head.

U.S. Pat. No. 3,835,861 discloses a surgical head clamp having three head engaging pins with two of the pins on a bracket and a third pin on a moveable pin carrier in which the moveable pin is held on a threaded pin carrier so finer adjustments in the relationship of the head engaging pins to the patient can be made.

U.S. Pat. No. 4,169,478 also discloses a surgical head clamp with three head engaging pins which is similar to that shown in U.S. Pat. No. 3,835,861. The head clamp includes a mechanism to rotate the bracket containing the two pins and reposition the head of the patient without releasing the head engaging pins from the patient's skull. The mechanism disclosed in U.S. Pat. No. 4,169,478 to prevent rotation employs interlocking teeth on stop members which are forced into engagement by ball actuators. The ball actuators move from dished sockets in the unlocked position to the lands between the dished sockets in the locket position. Upon repeated use and upon repeated sterilization, there is a tendency for foreign particles and debris to accumulate in the dished sockets or on the lands which prevent the positive locking of the bracket.

Although the surgical head clamp disclosed in U.S. Pat. No. 4,169,478 does offer certain advantages to the physicians, the problem exists in that the bracket can be inadvertently turned which may cause the head to move in the bracket and could cause injury to the patient. The weight of the patient in certain operating positions could exert a force against the bracket which might cause the bracket to turn if the ball actuators are not firmly positioned on the lands on the actuator disk.

The copending application Ser. No. 921,867, filed Jul. 28, 1992, discloses a head clamp which employs index pins between a rotatable bracket and the frame of the head clamp to prevent inadvertent rotation of the bracket. However, the bracket cannot be adjusted when the head engaging pins are engaging the patient's head. The patient's head must be disengaged from the pins before the bracket can be rotated.

BRIEF SUMMARY OF THE INVENTION

The head clamp of the present invention provides the flexibility of the device described in U.S. Pat. No. 4,169,478 mentioned above but prevents the inadvertent rotation of the bracket. The present head clamp includes two head engaging pins secured to a rocker arm on a bracket and a third head engaging pin which is held in a movable pin carrier. The present head clamp can be adjusted to reposition the patient's head without disengaging the head engaging pins from the patient but the present head clamp does have a positive locking mechanism to prevent inadvertent rotation of the bracket. The locking mechanism also may be visually inspected to insure that bracket is positively locked s it will not rotate.

The present head clamp employs ball actuators as disclosed in U.S. Pat. No. 4,169,478 to allow the bracket to be rotated without releasing the head engaging pins from the patient's head. The disclosure of said U.S. Pat. No. 4,169,478 is incorporated herein by reference. The head clamp of the present invention also provides a safety lock mechanism including a safety locking mechanism that can be unlocked to provide for the rotation of an operating handle, and the rotation of a rocker arm to allow the patient's head to be repositioned without disengaging the head engaging pins from the patient's head. When the patient's head has been repositioned, the safety locking mechanism can be locked to prevent inadvertent rotation.

The head clamp of the present invention provides the adjustment capability of the head clamp disclosed in U.S. Pat. No. 4,169,478 and also provides the ability to prevent the rotatable bracket of the head clamp from inadvertently rotating. This is accomplished by employing a safety locking pin as a secondary lock to positively lock the rotatable bracket of the head clamp in position when the operating handle is in the locked position.

BRIEF DESCRIPTION OF THE DRAWINGS

In the drawings.

FIG. 3 is an end view of the operating handle.

FIG. 4 is a detailed view partially in section of the locking handle and safety locking pin of the present invention as taken along line 4—4 of FIG. 3.

FIG. 5 is a cross sectional view of the operating handle in the locked position.

DETAIL DESCRIPTION OF THE INVENTION

Figure 1:
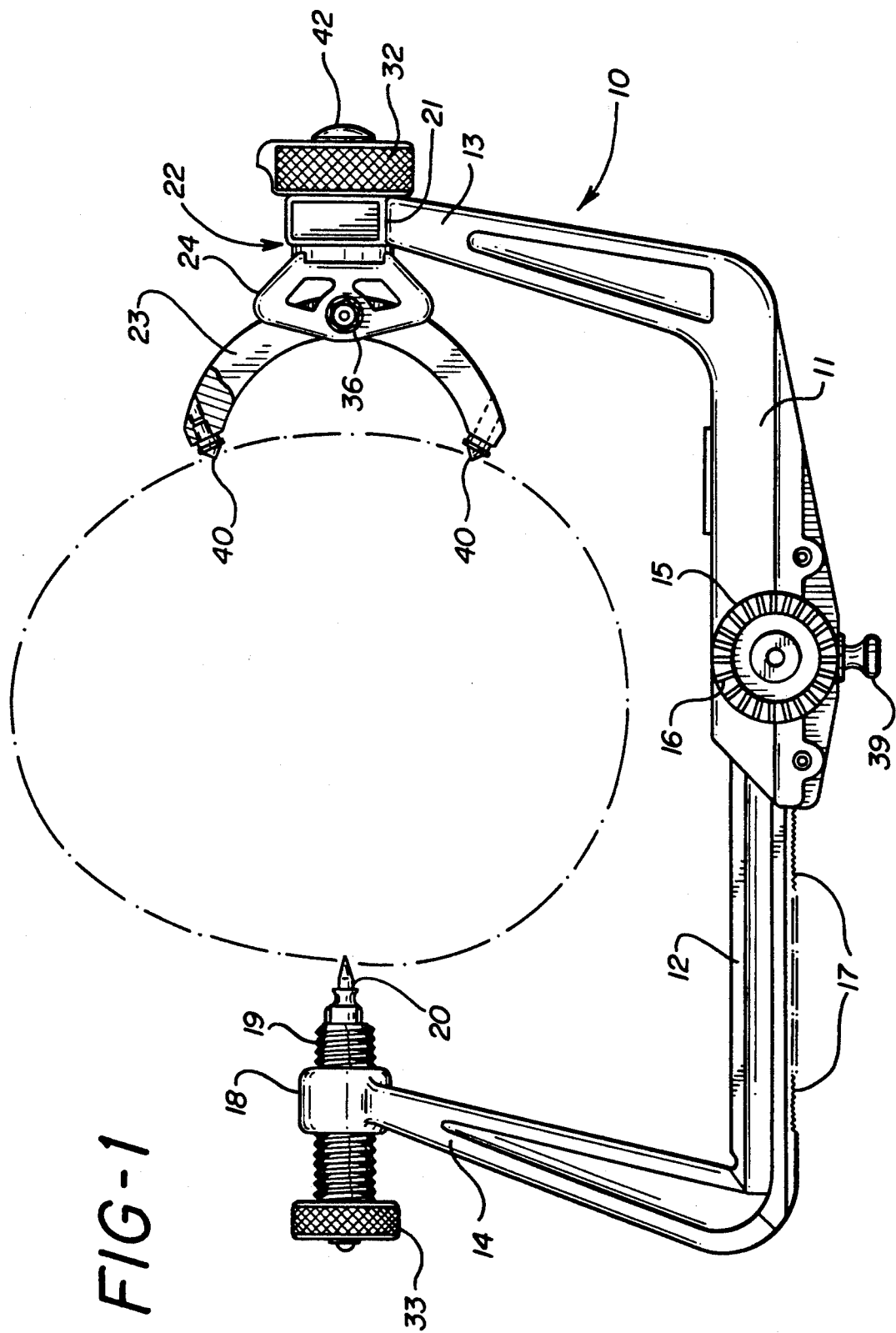
FIG. 1 is a plan view of the surgical head clamp in the present invention showing the relative position of the head in dash lines.

The basic skull clamp of the present invention as shown in FIG. 1 is similar to the clamp which is shown in U.S. Pat. Nos. 3,835,861 and 4,169,478. The clamp 10 includes a main fixed section 11 and a ratchet section 12. These sections are connected in a telescoping relationship with the ratchet section 12 being capable of telescoping into the fixed section 11. The ratchet section 12 has a number of teeth 17 which can engage teeth (not shown) on a plunger lock 39 to lock the ratchet section the fixed section of the clamp. On fixed section 11 there is an arm 13 which terminates in a boss 21 which has a hexagonal interior configuration. An arm 14 on ratchet section 12 terminates in an internally threaded boss 18 to receive a pin carrier 19. The pin carrier 19 has a knob 33 at one end and a pin receiving bore at the other end. A head engaging pin 20 is seated in the bore.

The head clamp is secured to the operating room table through a sunburst clamp 15 which has teeth 16 to engage matching teeth on a support, (not shown), which would be affixed to the operating room table.

Figure 2:
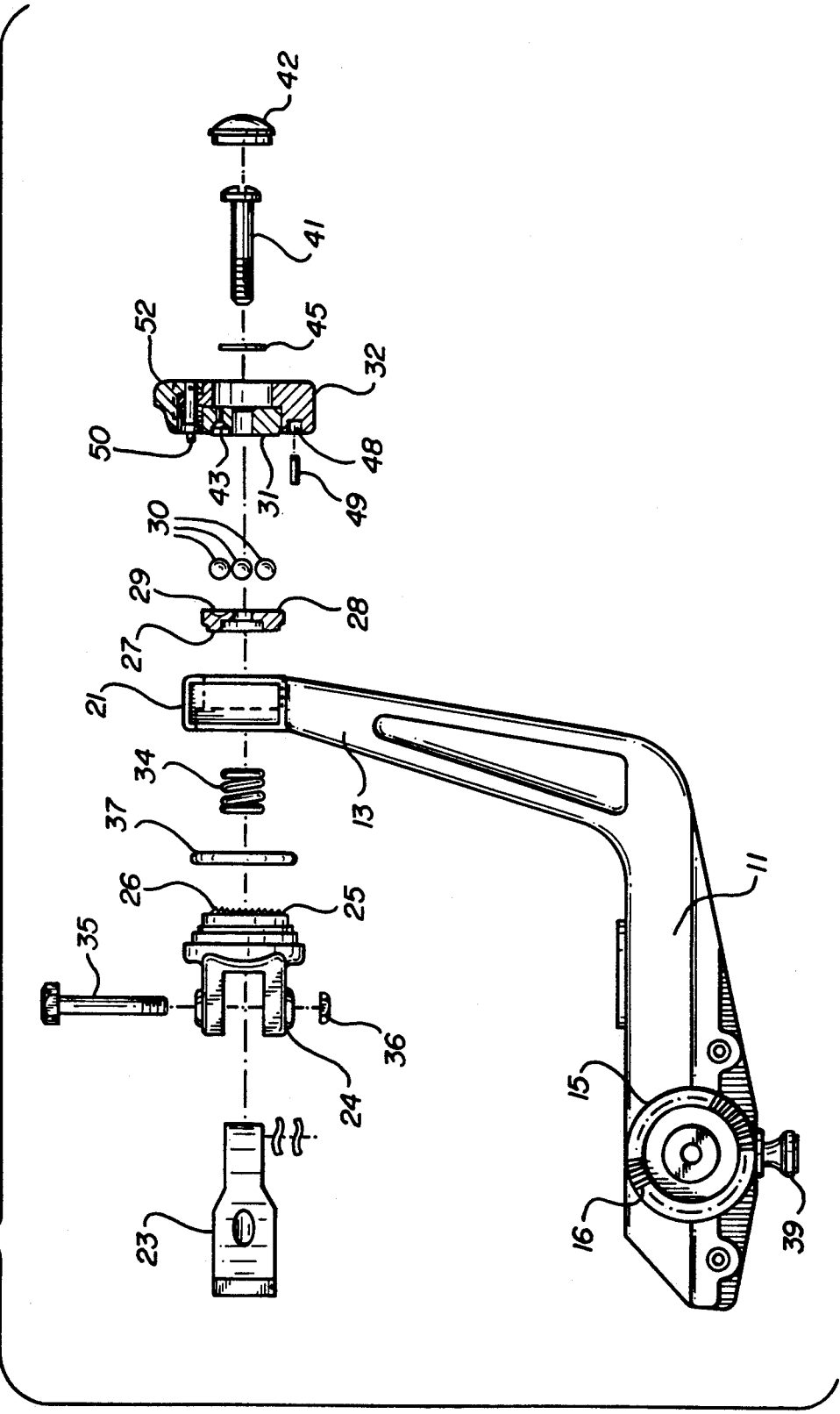
FIG. 2 is an exploded view of a portion of the head clamp shown in FIG. 1, showing the details of the rotating and locking mechanism of the present invention.

As shown in FIG. 1 and FIG. 2, the fixed arm section 13 terminates in a boss 21. This boss has a hexagonal opening, not shown, into which the operating handle and locking mechanism, shown in an exploded view in FIG. 2, is mounted. A rotatable bracket 24, mounting a rocker arm 23, is affixed to the locking mechanism generally shown as 22. There are bores at each end of the rocker arm to receive the head engaging pins 40. The bracket 24 is capable of rotation to adjust the position of the patient's head without removing the head engaging pins 20 and 40 from the patient's head.

The locking mechanism is similar to that shown in U.S. Pat. No. 4,169,478 and is depicted in an exploded view in FIG. 2. In FIG. 2 the rocker arm 23 and the rotatable bracket 24 have been turned 90° from the position shown in FIG. 1.

The rocker arm 23 is held to the rotatable bracket 24 by a single bolt 35 secured with a nut 36. As the rocker arm is held with a single bolt 35, it is capable of pivoting to adjust to the configuration of the patient's skull.

The end of the rotatable bracket 24 opposed to the end to which the rocker arm 23 is affixed contains a ring gear 25 which has teeth 26 which engage teeth 27 on a moveable ring gear 28. The moveable ring gear 28 is provided with three dished sockets 29 on the face opposite the teeth 27. Dished sockets 29 on the ring gear 28 are sized to receive one of three ball actuators 30. There are also dished sockets 43 in the actuator disk 31 in the operating handle 32. The ball actuators 30 rest in the dished sockets 29 of the movable ring gear 28 and the dished sockets 43 of the actuator disk 31 when the operating handle 32 is in the unlocked position. When the operating handle 32 is rotated to lock the bracket, the ball actuators are moved out of the dished sockets and onto the lands 44 between the dished sockets, as shown in FIG. 3. This movement forces the movable ring gear 28 to move against the pressure of the spring 34 and engage the teeth 27 on the moveable ring gear 28 with the teeth 26 on the ring gear 25 and thereby prevent rotation of the bracket 24 which is affixed to the ring gear 25. There is a circular 0-ring gasket 37 made from polytetraflouroethylene of a similar material fitted against the rotatable bracket 24 and the boss 21. The gasket 37 prevents fluids from entering into the locking mechanism during the surgical procedure. The rotatable bracket is affixed to the boss 21 by a bolt 41 which extends through a washer 45 and through the operating handle 32 and the moveable ring gear 28, and into threaded openings in the ring gear 25 and the rotatable bracket 24. The head of the bolt 41 can be covered with a cap 42 to provide an improved appearance to the device.

The operating handle 32 has a pin receiving slot 48 to receive a pin 49 which is secured to the boss 21. The pin 49 can move in the pin receiving slot 48, which extends around an arc of approximately 60° on the face of the operating handle 32, when the handle is rotated. When the pin is positioned at one end of pin receiving slot 48, the bracket 24 can be rotated. When the pin is positioned at the other end of the slot, the bracket is locked as shown in FIG. 4. At a point approximately 180° away from the one end, the locking end, of the pin receiving slot opening 48, there is a safety locking pin 50 mounted on the upper surface of the operating handle 32. The locking pin is attached to a locking slide 52 and is biased into a locked position by the spring 54. As shown in FIG. 5, there is a corresponding opening 47 on the boss 32 to receive the locking pin 50. As shown in FIG. 3, there is a dovetail slot 60 in the operating handle 32. There is a corresponding dovetail 62 on the locking slide 52 to provide slidable mounting of the locking slide 52 to the operating handle 32. The use of the safety locking pin prevents the inadvertent movement of the operating handle 32 which could cause the rotating of the bracket 24 and possible injury to a patient. The safety locking pin can only be seated in the opening 47 in the boss 21 when the operating handle 32 is in the locked position. The locking slide 52 extends outwardly beyond the outer face of the operating handle when the locking slide 52 is not in the locked position. The operating room staff can note the position of the slide to determine if the operating handle is in the locked position.

There are channels 55 at the base of the dished sockets 43. The channels extend through the actuator disk 32. The channels provide an opening or passageway for fluid to be drained and removed from the dished sockets during the vacuum cycle of a sterilization process used to sterilize the head clamp prior to use. This prevents the build up of mineral scale in the dished sockets which could interfere with the operation of the ball actuators to place the bracket 25 in a locked position.

In use, the patient's head would be affixed to the head clamp by positioning the head between the fixed arm 13 and the ratchet section of the arm 14. The ratchet section would then be telescoped into the fixed section so that the locking pins would engage the patient's skull. The pin carrying knob 33 could then be rotated to ensure the proper contact of the pin 20 with the patient's skull. In the event that it would be desirable to rotate the patient's head, the locking slide 52 would be moved outwardly which would carry the locking pin out of the opening 47 in the fixed arm boss 21. The operating handle could then be rotated from the locking position to the unlocking position which would move the ball actuators into the recesses formed by the alignment of the dished sockets 29 is the movable ring gear and the dished sockets 43 in the actuator disk 31. This would release the spring 34 and would then exert a force on the moveable ring gear 28 to separate the teeth 26 from the teeth 27. The bracket 24 would then be free to rotate to reposition the patient's head.

When the patient's head is in the proper position the operating handle would be turned until it had moved to a locked position. This movement will move the ball actuators out of the recesses formed by the dished sockets 29 and 43 unto the lands 44 and force the teeth 27 on movable ring gear 28 into engagement with the teeth 26 on the ring gear 25. The safety locking pin 50 could then engage the opening 47 in the boss 21. This locking pin ensures that the operating handle is in the locked position and prevents the inadvertent rotation of the operating handle 32 and the bracket 24. If the locking pin 50 is not fully seated in the opening 47, the slide 52 will extend beyond the outer face of the operating handle 32.

We claim:

1. In a surgical head clamp including a frame, a first head engaging pin supported on the frame, a bracket rotatably supported on the frame with the axis of rotation aligned with and spaced from the first head engaging pin, second and third head engaging pins mounted on the bracket, means for advancing the first head engaging pin axially toward the bracket to cause the head engaging pins to engage the head, the first head engaging pin being aligned with the axis of rotation of the bracket, a fixed ring gear on the bracket having teeth on its surface a moveable ring gear having teeth adapted to engage the teeth on the fixed ring gear, a rotatable operating handle, actuators positioned between one surface of an actuator disk affixed to the operating handle and said movable ring gear, said actuators capable of moving the moveable ring gear into engagement with the fixed ring gear upon rotation of the operating handle; the improvement comprising a safety locking pin mounted on the operating handle, an opening in the frame adjacent to the operating handle to received the safety locking pin, and thereby prevent rotation of the operating handle when the pin is in said opening.

2. The surgical head clamp of claim 1 in which the safety locking pin is attached to a locking slide which is slideably mounted in a slot on the periphery of the operating handle, and has a length dimension which is as least equal to the thickness of the operating handle.

3. The surgical head clamp of claim 2 in which the slot in the operating handle is a dovetail shape.

4. The head clamp of claim 1 in which there are dished sockets in the movable ring gear and an inner surface of the actuator disk to provide a recess for the actuators, an opening in the base of each of the dished sockets in the actuator disk to provide a passageway for fluid to be removed from said dished sockets.

* * * * *